(12) United States Patent
Kubiak (10) Patent No.: US 9,535,002 B2
(45) Date of Patent: Jan. 3, 2017

(54) DEVICE FOR INSPECTING A MATERIAL PROVIDED WITH A COATED SURFACE AND RELATED METHOD

(71) Applicant: ISRA SURFACE VISION GMBH, Dortmund (DE)

(72) Inventor: Rolf Kubiak, Dortmund (DE)

(73) Assignee: ISRA SURFACE VISION GMBH, Herten (DE)

( * ) Notice: Subject to any disclaimer, the term of this patent is extended or adjusted under 35 U.S.C. 154(b) by 31 days.

(21) Appl. No.: 14/599,741

(22) Filed: Jan. 19, 2015

(65) Prior Publication Data
US 2015/0204778 A1  Jul. 23, 2015

(30) Foreign Application Priority Data
Jan. 20, 2014 (DE) .................. 10 2014 100 594

(51) Int. Cl.
| | |
|---|---|
| *G01J 3/46* | (2006.01) |
| *G01N 21/25* | (2006.01) |
| *G01J 3/50* | (2006.01) |
| *G01N 21/84* | (2006.01) |
| *G01N 21/896* | (2006.01) |

(52) U.S. Cl.
CPC .............. *G01N 21/251* (2013.01); *G01J 3/50* (2013.01); *G01N 21/8422* (2013.01); *G01N 21/896* (2013.01); *G01N 2021/8427* (2013.01); *G01N 2201/061* (2013.01)

(58) Field of Classification Search
CPC ............. G01N 21/251; G01J 3/50; G01J 3/51; G01J 3/524; G01J 3/46; G01J 3/02
USPC .................................... 356/402–425
See application file for complete search history.

(56) References Cited

U.S. PATENT DOCUMENTS

| | | | |
|---|---|---|---|
| 5,396,080 A | 3/1995 | Hannotiau et al. | |
| 5,887,077 A * | 3/1999 | Bongardt | G01J 3/50 382/149 |
| 7,369,240 B1 | 5/2008 | Abbott et al. | |
| 7,551,274 B1 * | 6/2009 | Wornson | G01N 21/896 356/239.1 |
| 2007/0258093 A1 | 11/2007 | Sieck et al. | |

FOREIGN PATENT DOCUMENTS

| | | |
|---|---|---|
| DE | 4331355 | 3/1994 |
| DE | 19509345 | 9/1996 |
| EP | 2390656 | 11/2011 |
| JP | 2004144545 | 5/2004 |
| WO | WO2011/075212 | 6/2011 |

* cited by examiner

*Primary Examiner* — Abdullahi Nur
(74) *Attorney, Agent, or Firm* — Michael J. Striker (57) ABSTRACT

A device for inspecting a material with a coated surface includes a light source disposed above the surface that emits light in a wavelength range, at least one first camera for determining a color value of detected light reflected from the surface and an evaluation device. The first camera is disposed above a line located on the surface and configured with a first aperture to detect light from a first point of the line at a first viewing angle and light from a second point separate from the first point at a second viewing angle. The first camera determines a first color value of the first point light and a second color value of the second point light and the evaluation device compares the first and second color values or a color value difference with a predefined color setpoint value or predefined color setpoint value range.

14 Claims, 5 Drawing Sheets

DEVICE FOR INSPECTING A MATERIAL PROVIDED WITH A COATED SURFACE AND RELATED METHOD

CROSS-REFERENCE TO A RELATED APPLICATION

The invention described and claimed hereinbelow is also described in German Patent Application DE 10 2014 100 594.5, filed on Jan. 20, 2014. The German Patent Application, the subject matters of which is incorporated herein by reference, provides the basis for a claim of priority of invention under 35 U.S.C. 119(a)-(d).

BACKGROUND OF THE INVENTION

The present invention relates to a device for inspecting a material provided with a coated surface, preferably glass, and a related method.

Surface coatings on materials, in particular glass, are intended to improve or modify the properties of these materials, for example, as antireflective coatings or thermal barrier coatings. Surface coatings comprise thin metal layers or dielectric layers, for example. Coated surfaces, in particular those having a plurality of layers, form interferences (interference layers), which cause the surfaces to exhibit different colors from different viewing angles. These colors are predefined by the thickness of the interference layers.

For large glass surfaces, e.g., glass facades, such color effects can function as a design. In this connection, the objective (possibly in addition to other functions of these layers) is to have the entire glass facade appear homogeneous in a single, predefined color (often green or blue), wherein deviations from these colors are perceived to be unattractive. This means that the light reflected by the material surface has a certain color, i.e., a certain spectrum of wavelengths. For large surfaces of this type, it is furthermore desirable that the facade color not change, even when the viewing angle changes, for example when the observer passes by this facade.

When such materials having coated surfaces are produced, defects can occur that cause the color of the surface to no longer appear homogeneous. A distinction is made in this case to two different types of defects, namely defect type 1, in which the color changes when viewed from a constant viewing angle and defect type 2, which results when the surface has the same color under a constant viewing angle, but the color of the surface changes when the viewing angle changes. This effect always occurs, in principle, with multiple coatings, although the goal is to minimize this defect type to the greatest extent possible by maintaining certain layer thicknesses. The reason for the differentiation into the two aforementioned defect types is that the two defect types have different causes and require different countermeasures in an effort to prevent their occurrence. Therefore, it is also important to know which defect type is present when a color deviation occurs.

Up to now, the inspection of the surfaces was carried out using a plurality of spectrometers, which determine the color of the light reflected on the surface at at least two viewing angles. Since the color of only a small region of the surface can be determined in each spectrometer, the surface must be scanned in a pointwise manner using these spectrometers. This is highly complex and time-consuming, however, and it would be desirable to find a simpler and more cost-favorable solution for inspecting the color of coated surfaces.

In addition to the above-described color defects, it also is possible for a plurality of other defects to occur during the production of such surfaces that do not affect the color, such as optical defects, bubbles, inclusions and scratches. Nowadays, high-quality surfaces, for example, glass that is used to build glass facades, are nearly always subjected to an optical inspection for these other defects. These inspection systems operate with high resolution since the defects being sought are small. The color information obtained from the reflected light is not required for the investigation of such defects, and therefore the optical recording devices used to detect such defects do not capture the color information.

SUMMARY OF THE INVENTION

The present invention overcomes the shortcomings of known arts, such as those mentioned above.

The invention provides a device with which the color inspection of a material provided with a coated surface is carried out in a simple and cost-favorable manner and method for inspecting the color of coated surfaces though the use of such device.

In an embodiment, the device comprises a light source disposed above the surface of the coated material that emits light in a predefined wavelength range in the direction of the surface and at least one first camera set up to determine a color value of the detected light. The first camera is disposed above a line, which is located on the surface, is tilted relative to the light source, and has a first (large) aperture such that light from the light source that is reflected by a first point of the line is detected at a first viewing angle and the light reflected by a second point of the line, which is spaced apart from the first point, is detected separately at a second viewing angle. The at least one first camera determines a first color value of the light reflected by the first point and a second color value of the light reflected by the second point.

An evaluation device is connected to the first camera and compares the first color value and the second color value, or the difference between the two, with a certain predefined color setpoint value or with a certain predefined color setpoint value range. Within the scope of the present invention, the first and the second viewing angle can be the same or different.

The line of reflected light from the light source that is scanned by the camera at one point in time, by which at least the first and the second point, i.e., a plurality of points, of the surface are detected simultaneously, also is referred to in the following as an inspection line or a scanning line.

The device makes it possible, while using only one camera, to determine whether color deviations are present by comparing the first color value and the second color value of two different points of the inspection line with one another, because the points are observed by the camera at different viewing angles. If color deviations are found, it is highly likely that defect type 2 is present.

In an embodiment, the evaluation device is set up such that the difference of the first color value of the first point of the inspection line and the second color value of the second point of the inspection line is compared with the certain predefined color setpoint value or the certain predefined color setpoint value range. The first point and the second point are observed by the camera at the same or approximately the same viewing angle. That is, the two points are spaced apart, wherein the first viewing angle and the second viewing angle are the same or approximately the same and wherein the viewing angles are measured in a different direction along the inspection line. This method can be carried out with one or more pairs of points, each of which are observed at the same or approximately the same viewing angle. Same allows for determining that defect type 1 is very likely present, but that defect type 2 cannot be ruled out.

In order to permit reliable detection of defect type 1 as well, at least one second camera is additionally provided that also is set up to detect a color value of the detected light. The second camera is disposed above the inspection line located on the surface and is tilted relative to the light source. The second camera has a second (large) aperture such that light from the light source that is reflected by each point of the inspection line is preferably detected simultaneously by the first camera and by the second camera, wherein the first camera and the second camera each determine the color value of the light reflected by each point of the inspection line. The evaluation device connected to the first camera and the second camera uses the thusly determined color values of the first camera and the second camera at each point of the inspection line to perform a comparison with the certain predefined color setpoint value or the certain predefined color setpoint value range.

The device therefore comprises one first camera and at least one second camera, which detect, from each point of the inspection line, a color value of the first camera and a color value of the second camera of the light from the light source that is reflected by the surface. Both cameras have such a large aperture that the light reflected by each point of the inspection line can be detected by the first camera and by the second camera.

The first camera and the second camera are disposed next to one another such that the light from the light source that is reflected by each point of the inspection line is recorded by each camera at a different viewing angle. Depending on the arrangement of the cameras, the situation can arise in which the viewing angle of the first camera differs not at all or only very slightly from the viewing angle of the second camera. In this case, it is advantageous to provide a third camera for such a range of the inspection line, the third camera detecting the points of the region of the inspection line at a third viewing angle. This procedure is described in detail further below.

In the inventive device and method, the viewing angle is considered to be the viewing direction of the particular camera onto the corresponding point of the inspection line relative to the normal line on the surface that is disposed at this point. Alternatively, it is possible to use the angle of the viewing direction of the particular camera onto the corresponding point of the inspection line, projected onto the plane that passes through the normal line on the surface that is disposed at this point and the inspection line.

As used herein, the expression "tilted (slanted) relative to the light source" is intended to mean that the camera is disposed such that it sees or captures the specular reflection of the light emitted from the light source on the coated surface in the region of the inspection line.

The evaluation unit, to which the color values from each point of the inspection line are transferred (the color values having been determined by the first camera and by the at least one second camera), compares the color values of the light that is reflected by each point of the inspection line and is detected by the second camera with a certain predefined color setpoint value or a certain predefined color setpoint value range in order to determine whether a color deviation is present. With this method it is possible, in particular, to determine whether a color deviation according to defect type 2 is present. If the color values of the points that have the same viewing angle with respect to the first and the second camera (either relative to the same camera or relative to the various cameras) also are analyzed, then it is also possible to check for the presence of defect type 1. As an option, the evaluation device also evaluates the color value of the light reflected by various points of the inspection line depending on the associated viewing angle.

In order to obtain color values at a first viewing angle and a second viewing angle for all points of the inspection line (the viewing angles of which have the greatest possible difference), it is advantageous if at least three cameras are provided and preferably disposed next to one another above the inspection line. The apertures of the cameras are disposed so as to overlap such that light reflected by each point of the inspection line is detected by at least two of the three cameras, at a different viewing angle by each of the two cameras.

In addition, it is advantageous when the first camera and the at least one second camera are disposed on a common carrier. As a result, the device according to the invention is particularly compact, which is advantageous since space in the production lines is very limited and every additional inspection site is expensive.

Furthermore, it is advantageous when the first camera and/or the at least one second camera are each formed as a line scan camera or an area scan camera, wherein the line scan camera comprises a plurality of light detection elements disposed in a row and the area scan camera comprises a plurality of light detection elements (e.g., photodiodes) disposed in an area. The camera line of a line scan camera or a line of an area scan camera can simultaneously detect the reflected light of at least one region of an inspection line. The color value of the reflected light of a plurality of inspection lines is recorded simultaneously by an area scan camera.

The line scan camera and the area scan camera are color cameras that determine the color value of each detected point. In this connection, each light detection element (e.g., each photodiode) of the camera records a color value for a certain point of the inspection line, wherein the extension of the "point" along the inspection line is determined by the device-specific resolution of the camera. A certain viewing angle is assigned to each point of the inspection line that reflects light, wherein the light is captured by a single light detection element. The viewing angle results from the viewing direction of the camera onto this point. Therefore, different viewing angles are assigned to all points of the inspection line, which are recorded simultaneously by all light detection elements of a line scan camera. The same applies similarly for an area scan camera.

In order to obtain a reliable finding regarding the quality of the material or the surface coating with respect to defect type 2 in particular, it is advantageous when the difference of the first viewing angle and the second viewing angle is as great as possible, in particular when the viewing angle difference is at least 10°, preferably at least 15°, most preferably at least 20°, also when at least two cameras are used to observe one point.

An efficient and exact color inspection of large coated surfaces is possible when the material can be moved relative to the first and the second camera and relative to the light, source in the direction of a feed direction transversely to the inspection line, wherein the light source and/or the first camera and/or the second camera are preferably tilted in the feed direction or counter to the feed direction in order to detect the specular reflection of the light source. The angle of inclination of the camera relative to the normal line on the coated surface is preferably at least 20°.

The light source is preferably designed as a substantially linear light source, which extends parallel to the inspection line and emits white light. Most preferably, a light source is used that comprises one row or a plurality of rows of LEDs disposed one behind the other in the feed direction.

When the inspection line covers the entire width of the material perpendicularly to the feed direction, the entire surface is scanned easily and rapidly.

As explained above, it is advantageous when at least one third camera is provided in the device, which is set up to determine a third color value of the detected light, wherein the third camera is disposed above the inspection line and it tilted relative to the light source. The third camera has a third aperture such that the reflected light of the light source (18) can be additionally detected and the associated color value can be determined in a certain range of the inspection line, at least for the points of the inspection line in a certain range of the inspection line.

The evaluation device compares the viewing angle of the third camera with the viewing angle of the first camera and/or the viewing angle of the second camera for each point of the determined region of the inspection line and, for the corresponding point of the determined region, uses those two color values of the first camera, the second camera and the third camera for comparison with the certain predefined color setpoint value or the certain predetermined color setpoint value range for which the difference of the associated viewing angle is greatest.

The comparison of the viewing angle in each point of the inspection line is used to determine the respective minimum and maximum viewing angles of all cameras that have determined color values in the respective point. The evaluation device then utilizes the color values of the two cameras for the comparison with the color setpoint value or the color setpoint value range, the associated camera of which has the minimum viewing angle and the camera of which has the maximum viewing angle.

In an embodiment, the evaluation device determines, in each point of the inspection line, a color value difference of two color values of two certain predefined cameras (i.e., the first, second or third camera such that the two cameras having the greatest viewing angle difference), which observe the light reflected by this point and compares this color value difference with a certain predefined color value difference setpoint value or a certain predefined color value difference setpoint range, optionally dependent on the difference of the associated viewing angles.

This evaluation method is advantageous, in particular, for identifying a type 2 color defect and is faster than an individual evaluation of the color values of the two cameras for each point of the inspection line. Such device according to the invention is preferably used when it is known that the coated surface to be investigated has the greatest color differences at certain angles, and therefore only certain small angular ranges need to be examined in greater detail.

The method according to the invention for inspecting a material provided with a coated surface, preferably glass, requires a light source that is disposed above the surface and emits light in a predefined wavelength range in the direction of the surface, and at least one camera, wherein the first camera is set up to determine a color value of the detected light. The first camera is disposed above an inspection line located on the surface, at a slant relative to the light source, and has a first (large) aperture. The method of using the device comprises:

separately detecting, by the first camera, the light from the light source that is reflected by a first point of the inspection line at a first viewing angle and the light from the light source that is reflected by a second point of the inspection line, which is spaced apart from the first point, at a second viewing angle, wherein the first camera determines a first color value of the light reflected by the first point and a second color value of the light reflected by the second point; and using an evaluation device connected to the first camera, comparing the first color value and the second color value or the difference between the two with a certain predefined color setpoint value or a certain predefined color setpoint value range.

The method is easy to carry out and has the above-described advantages. The method is suitable for identifying a color deviation or color defect of defect type 1 with high probability when points of the inspection line that are observed by the camera at the same viewing angle are used as the basis for the color inspection. Defect type 2 cannot be ruled out with this embodiment. If various points of the inspection line having different viewing angles are used for the color inspection and color deviations are identified, then the presence of defect type 2 can be determined only with high probability.

In a manner analogous to the statements provided above with respect to the device according to the invention, it is advantageous when at least one second camera is provided, wherein the second camera also is set up to determine a color value of the detected light, disposed above the inspection line located on the surface and at a slant relative to the light source and has a second (large) aperture. The first camera and the second camera preferably simultaneously detect light from the light source that is reflected by each point of the inspection line and, in each case, the color value of the light reflected by each point of the inspection line is determined and is compared by the evaluation device, with the certain predefined color setpoint value or the certain predefined color setpoint value range.

With respect to the method, it also is advantageous when the evaluation device additionally evaluates the color value of the reflected light of various points of the inspection line, independently of the associated viewing angle thereof, in order to determine the defect type 1. The viewing angle is therefore incorporated into the analysis and a check is carried out to determine whether the desired color value is obtained at a certain viewing angle.

In an embodiment of the method, at least one third camera is provided, which is set up to determine a third color value of the detected light, the third camera is disposed above the inspection line and at a slant relative to the light source, having a third (large) aperture and additionally detects the reflected light of the light source and determines the associated color value at least for the points of the inspection line in a certain range of the inspection line. The evaluation device compares the viewing angle of the third camera with the viewing angle of the first camera and/or the viewing angle of the second camera for each point of the certain region of the inspection line and, for the corresponding point of the certain region, uses those two color values of the first camera, the second camera and the third camera for the comparison with the certain predefined color setpoint value or the certain predefined color setpoint value range for which the difference of the associated viewing angle is greatest.

As explained above, this embodiment makes it possible to obtain a large viewing angle difference since it is possible to use the color value of the camera having the minimum viewing angle and the color value of the camera having the maximum viewing angle for the comparison with the predefined color setpoint value or the color setpoint value range, for each point of the inspection line.

As described above, it also is advantageous when the evaluation device determines a color value difference of two color values of two certain cameras that observe the light reflected from this point, at each point of the inspection line, and compares this color value difference with a certain predefined color value difference setpoint value or a certain predefined color value difference setpoint range, optionally additionally independently of the respective viewing angle.

The comparison of the first color value and/or the second color value and/or, optionally, the third color value with the color setpoint value or the color setpoint value range is carried out in the evaluation unit, preferably on the basis of the Lab color space, which is defined by the standard EN ISO 11664-4. This color space (color model) covers the range of perceptible colors and is designed on the basis of the color-opponent theory. The Lab color space is described by a three-dimensional coordinate system, wherein the "a" axis describes the green fraction or red fraction of a color, the "b" axis describes the blue fraction or yellow fraction of a color, and the "L" axis describes the brightness (luminance) of the color with values between 0 and 100. This color space was previously referred to as the CIELAB color space. For the comparison of the color values or the color difference values with the color setpoint value or the color setpoint value range or with the color value difference setpoint value or the color value difference setpoint value range, it may be necessary to convert the color values transmitted to the evaluation device from the first and/or the second camera and/or the third camera to the Lab color space.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
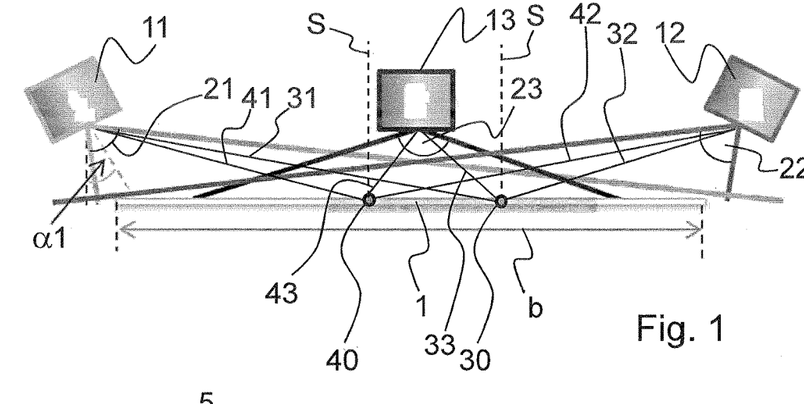
FIG. 1 depicts a first embodiment of a device according to the invention, in a view from the front.
Figure 2:
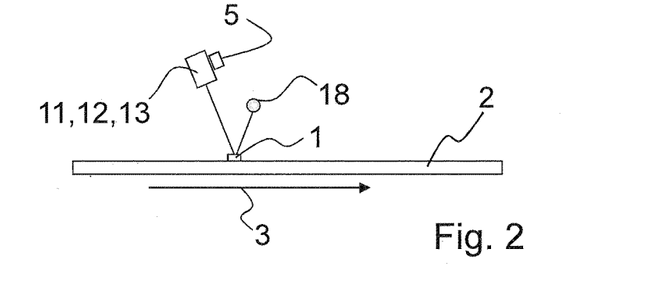
FIG. 2 depicts a view from the side for the FIG. 1 device.

The device depicted in FIG. 1 shows the inspection line 1 on the surface of the material, which is shown in FIG. 2, in the form of a glass 2 provided with a surface coating (e.g., an antireflective coating or a thermal barrier coating) and which is observed by a first camera 11, a second camera 12, and a third camera 13. The material 2 is moved in the moving direction indicated by the arrow 3 (see FIG. 2) relative to the fixed cameras 11, 12, 13 and the light source 18, which is disposed above the surface of the material 2 and is formed, for example, by a row of LEDs arranged parallel to the inspection line, wherein said LEDs emit white light. The inspection line 1 having the width b extends transversely to the moving direction and extends across the entire width of the glass 2 such that the entire surface of the glass 2 can be inspected with regard to the color of the reflected light. The cameras 11, 12 and 13 are each designed as color cameras and as line scan cameras.

As is evident in FIG. 1, the first camera 11 has a first aperture 21, the second camera 12 has a second aperture 22, and the third camera 13 has a third aperture 23. The first camera 11, the second camera 12 and the third camera 13 are disposed next to one another on a rod-shaped carrier 5 (see FIG. 2). The first camera 11 and the second camera 12 are tilted at a certain predefined angle (the angle α1 associated with the camera 11 is indicated in FIG. 1) relative to the normal line on the surface of the material 2 in the plane passing through the normal line and the inspection line 1. Each of these two cameras 11, 12 can therefore detect the reflection of the light that is emitted by the light source 18 and is reflected in each point of the inspection line 1 at a different viewing angle.

FIG. 2 shows that the cameras 11, 12, 13 are tilted relative to the moving direction 3 such that the reflection of the light emitted by the light source 18 can also be observed on the inspection line 1 by the cameras 11, 12, 13. At this point it should be pointed out that the inspection line 1 is located in the surface of the glass 2, which differs from the schematic depiction in FIG. 2, wherein the inspection line 1 preferably has a certain extension on the surface in the direction transversely to the inspection line 1 in order to compensate for height differences that the glass 2 can have on the surface thereof, and to permit a color inspection to be carried out despite such height differences. To this end, it is necessary that the light from the light source 18 that is reflected on the surface in the region of the inspection line reach the respective camera 11, 12, 13.

Each camera 11, 12 and 13 detects the light that is generated by the light source 18, which is disposed above the inspection line 1, and that is reflected on the surface of the glass 2. Since the first aperture 21 of the first camera 11 and the second aperture 22 of the second camera 12 are selected to be so large that these cameras 11, 12 can view every point of the inspection line 1, the color value of each point of the inspection line 1 can be detected by the cameras 11, 12 at two different viewing angles.

In addition, the third camera 13 is disposed in the middle region of the inspection line 1, wherein the third camera detects the color value of the light reflected by the surface of the glass 2 from the points of the inspection line 1 that are located within the aperture 23 of the third camera 13, at a third viewing angle.

For example, the first camera 11 sees a first point 30 of the inspection line 1 along a first line of sight 31, the second camera 12 sees the first point 30 along a second line of sight 32, and the third camera 13 sees this point along a third line of sight 33. The light reflected from the surface of the glass 2 is therefore detected by the first camera 11 at a first viewing angle, which is formed by the line of sight 31 with the normal line S in this point 30, by the second camera at a second viewing angle, which is formed by the line of sight 32 with the normal line S in this point 30, and by the third camera 13 at a third viewing angle, which is formed by the line of sight 33 with the normal line S in this point 30.

Correspondingly, the light reflected by a second point 40 of the inspection line 1 is detected by the first camera 11 at a viewing angle that is formed by a first line of sight 41 with the normal line S in this point 40, by the second camera 12 at a second viewing angle that is formed by the second line of sight 42 with the normal line S in this point 40, and by the third camera 13 at a second viewing angle that is formed by the third line of sight 43 with the normal line S in this point 40.

The color values determined by the cameras 11, 12, 13 for all points of the inspection line 1 are transmitted to the evaluation unit, which is not shown. This evaluation unit compares the color values determined for the respective points, i.e., the color values determined for the first point 30 and the second point 40, with the predefined color setpoint values or color setpoint value ranges, wherein such a color setpoint value range comprises, for example, a certain blue range or green range. If the color values determined by the cameras for all points of the inspection line are located in the predefined color setpoint value range, then the coated glass 2 is free of defects. If it is determined that deviations exist for at least one point of the inspection line, for which two color values are detected from two different viewing directions, by a comparison of these two color values for this point with the predefined color setpoint value or the predefined color setpoint value range, then a defect type 2 is present.

In addition, an analysis is carried out for at least one constant viewing angle to determine whether the determined color values are located in a color setpoint value or color setpoint value range that is predefined for the particular viewing angle or viewing angle range. In this manner it is determined whether a defect type 1 is present.

The comparison of the determined color values with the color setpoint value or the color setpoint value range is preferably carried out in the Lab color space. To this end, the color values are converted into a value according to the Lab color space by the particular camera 11, 12, 13 itself or this conversion is carried out before the comparison by the evaluation device.

Figure 4:
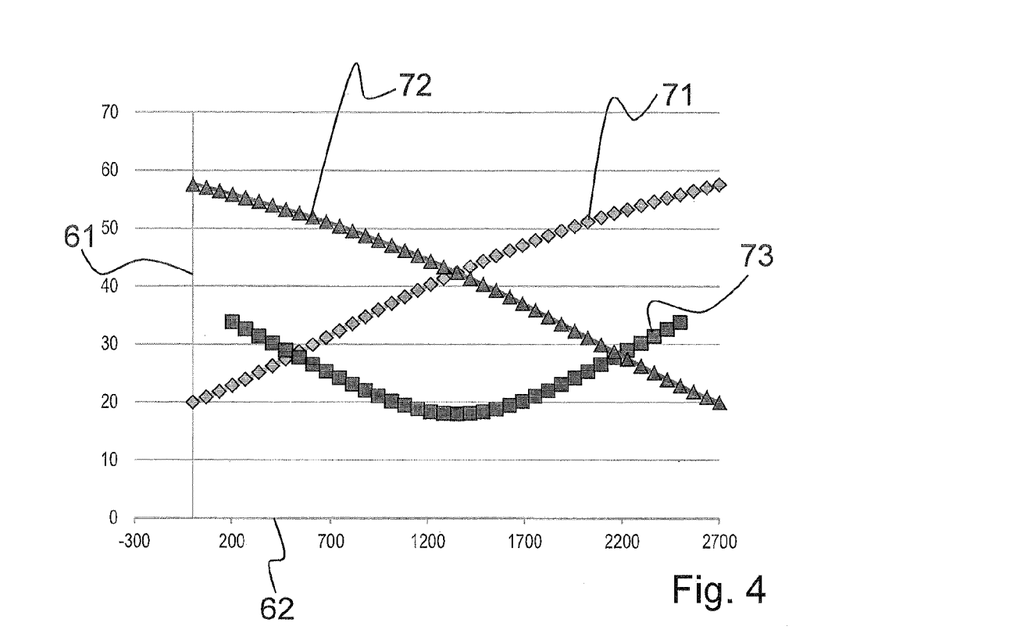
FIG. 4 presents a diagram depicting a course of the viewing angle of each camera of the first embodiment, depending on the location of the point on the inspection line.

FIG. 4 shows the viewing angle of the cameras (axis 61) depending on the position of the point on the inspection line 1 (see axis 62). The curve 71 shows that the viewing angle of the reflected light that is observed from the points of the inspection line 1 by the first camera 11 changes from an angle of approximately 20° for a point on the left side of the inspection line 1, shown in FIG. 1, to approximately 58° for a point on the right side of the inspection line 1, in FIG. 1. Correspondingly, the viewing angle for the camera 12 decreases from left to right along the inspection line 1 from approximately 58° to 20° (see curve 72). The middle viewing angle range detected by the third camera extends between approximately 18° and 35° (see curve 73).

Figure 5:
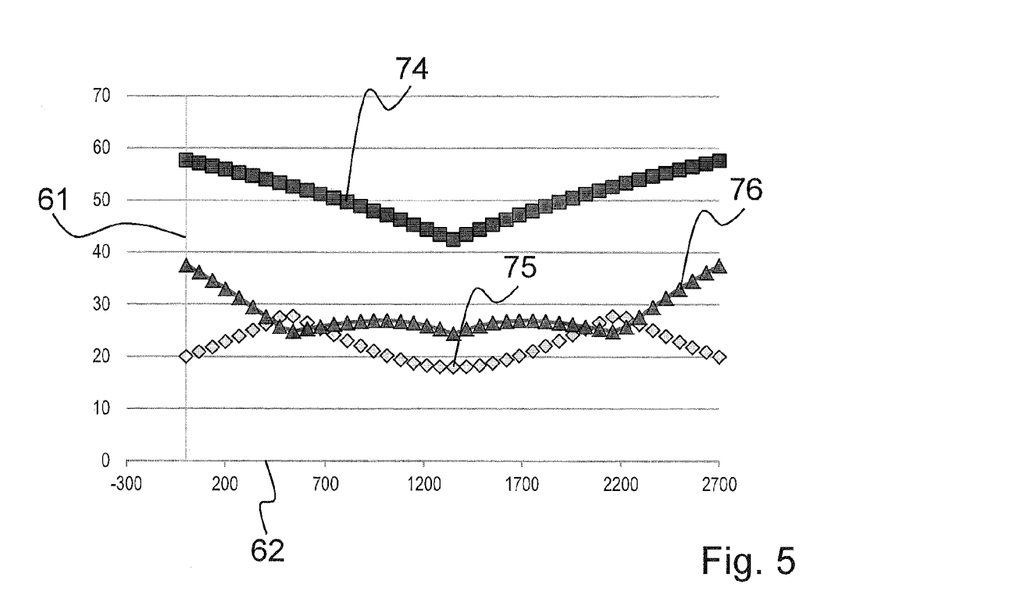
FIG. 5 presents a diagram based on the viewing-angle course for all cameras shown in FIG. 4, including the course of small viewing angles, the course of large viewing angles and the difference thereof, depending on the location of the point on the inspection line.

The diagram in FIG. 5 illustrates the evaluation on the basis of small and large viewing angles and on the basis of the viewing angle difference. To this end, the viewing angles of each camera 11, 12, 13 in each point are compared with one another by the evaluation device.

The curve 74 shows the respective largest (maximum) viewing angles in each point of the inspection line 1, which are located between approximately 58° and 42°, and which are generated in the left subregion by the second camera (see curve 72 in FIG. 4) and in the right subregion by the first camera (see curve 71 in FIG. 4). The smallest (minimum) viewing angles in each point of the inspection line 1, which are shown in curve 75 of FIG. 5, are formed in a first left region by the first camera (see curve 71 in FIG. 4), in a middle region by the third camera (see curve 73 in FIG. 4), and in a right region by the second camera.

In order to cover the largest possible viewing angle range, the color values of the camera associated with the particular viewing angle that form the largest viewing angle depicted in curve 74 are compared with the corresponding, predefined color setpoint value or the color setpoint value range, for each point of the inspection line 1. In an analogous manner, the color values of the camera associated with the particular viewing angle that form the smallest viewing angle depicted in curve 75 are compared with the corresponding, predefined color setpoint value or the color setpoint value range, for each point of the inspection line 1.

In a further embodiment, the viewing angle difference between the respective largest viewing angle depicted in curve 74 and the respective smallest viewing angle depicted in curve 75 is calculated, for each point of the inspection line 1. This yields the curve 76 in FIG. 5. Furthermore, the difference between the color values associated with the respective cameras is determined, i.e., the difference between the color values of the second camera and the first camera in a left region of the inspection line 1, the difference between the color values of the second camera and the third camera and then the difference between the color values of the first camera and the third camera in a middle region and the difference between color values of the first camera and the second camera in a right region. These differences are then investigated (optionally by referring to the respective viewing angle difference depicted in curve 76) to determine whether the color value differences are located in a predefined color value difference setpoint value range.

If a deviation of the difference between the respective color value for the largest viewing angle difference and the respective color value for the smallest viewing angle from the color value difference setpoint value or the color value difference setpoint value range is found at one point or several points of the inspection line, then a defect type 2 is present.

If the objective is to then determine whether defect type 1 is present, the color value must be determined for the same viewing angle of the first camera, the second camera and the third camera. For a certain viewing angle, the color inspection can be carried out for points of the inspection line at which, for example, the curves 74 and 75 in FIG. 5 are intersected by horizontal lines. The color inspection can be carried out for a plurality of sets of identical viewing angles that extend across the entire width of the inspection line, which can be illustrated by a parallel displacement of the intersection lines. The color values determined for the sets of identical viewing angles can be compared with the certain predefined color setpoint value or the certain predefined color setpoint value range in order to determine whether a defect type 1 is present anywhere across the entire width of the inspection line.

The statements made regarding the curve 75 also apply, with limitation, to the curve 74. However, for the viewing angles depicted in curve 74, the angular range is larger and only two cameras are used.

Figure 3:
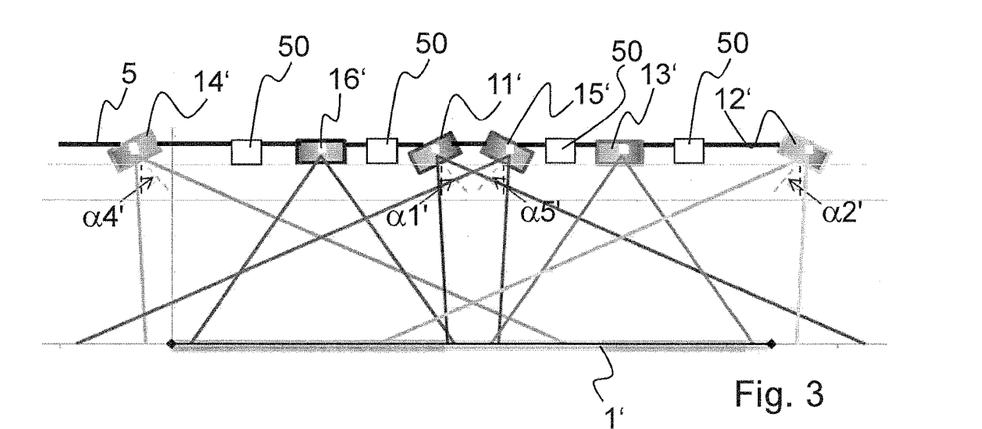
FIG. 3 depicts a second embodiment of a device according to the invention, in a view from the front.

FIG. 3 shows an embodiment of a device according to the invention comprising a first camera 11', a second camera 12', a third camera 13', a fourth camera 14', a fifth camera 15' and a sixth camera 16', which are disposed next to one another on a carrier 5 and detect the light, along the inspection line 1', that was emitted by the linear and white light source (not shown) and that was reflected by the surface of the coated glass 2.

Each camera is tilted at an angle relative to the normal line on the inspection line. For example, the first camera 11' is tilted at an angle α1', the second camera 12' is tilted at a second angle α2', the fourth camera 14' is tilted at an angle α4', and the fifth camera 15' is tilted at a fifth angle α5'. The inclination angles of the third camera 13' and the sixth camera 16' are not shown.

In a manner analogous to the FIG. 1 embodiment, all the cameras 11', 12', 13', 14', 15', 16' have large apertures, thereby enabling these cameras to detect the reflected light of a large region of the inspection line 1' at various viewing angles. The respective viewing angle range can be found in the diagram presented in FIG. 6, depending on the location.

Figure 6:
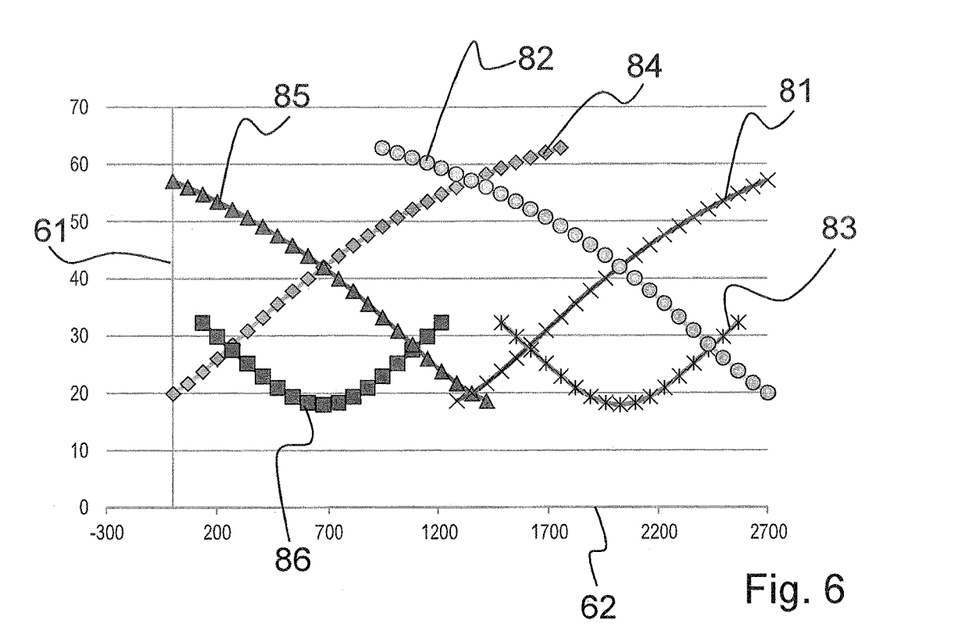
FIG. 6 presents a diagram based on the course of the viewing angle of each camera of the second embodiment (depicted in FIG. 3), depending on the location of the point on the inspection line.
Figure 7:
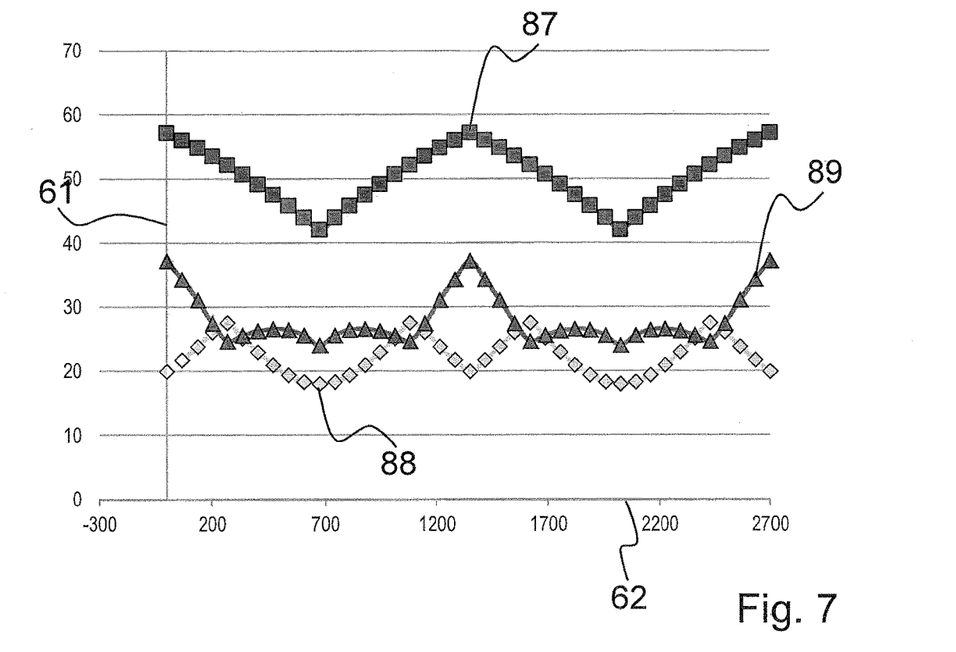
FIG. 7 presents a diagram based on the viewing-angle course for all cameras shown in FIG. 6, including the course of small viewing angles, the course of large viewing angles and the difference thereof, depending on the location of the point on the inspection line.

The viewing angle range of the first camera 11' is illustrated by the curve 81, the viewing angle range of the second camera 12' is illustrated by the curve 82, the viewing angle range of the third camera 13' is illustrated by the curve 83, the viewing angle range of the fourth camera 14' is illustrated by the curve 84, the viewing angle range of the fifth camera 15' is illustrated by the curve 85, and the viewing angle range of the sixth camera 16' is illustrated by the curve 86. In a manner analogous to the procedure that was described with reference to the diagram shown in FIG. 5, it also is possible, with this device according to the invention, to only use those color values of the camera, in a pointwise manner, for the comparison with a color setpoint value or a color setpoint value range that have a large viewing angle (cf. curve 87 in FIG. 7) and/or a small viewing angle (cf. curve 88 in FIG. 7) for a certain point of the inspection line 1'.

In a manner analogous to the above-described procedure, it is also possible to use only a difference between the color values for the large viewing angles shown in curve 87 and the small viewing angles shown in curve 88 (see curve 89 in FIG. 7) for the comparison with a corresponding color value difference setpoint value range.

Additional measuring devices 50 can be disposed on the carrier of the device according to the invention, as depicted in FIG. 3, wherein the measuring devices investigate the glass 2 for the presence of further defects, such as optical defects, bubbles, inclusions, and scratches, for example. High-resolution cameras are preferably used for this purpose.

Figure 8:
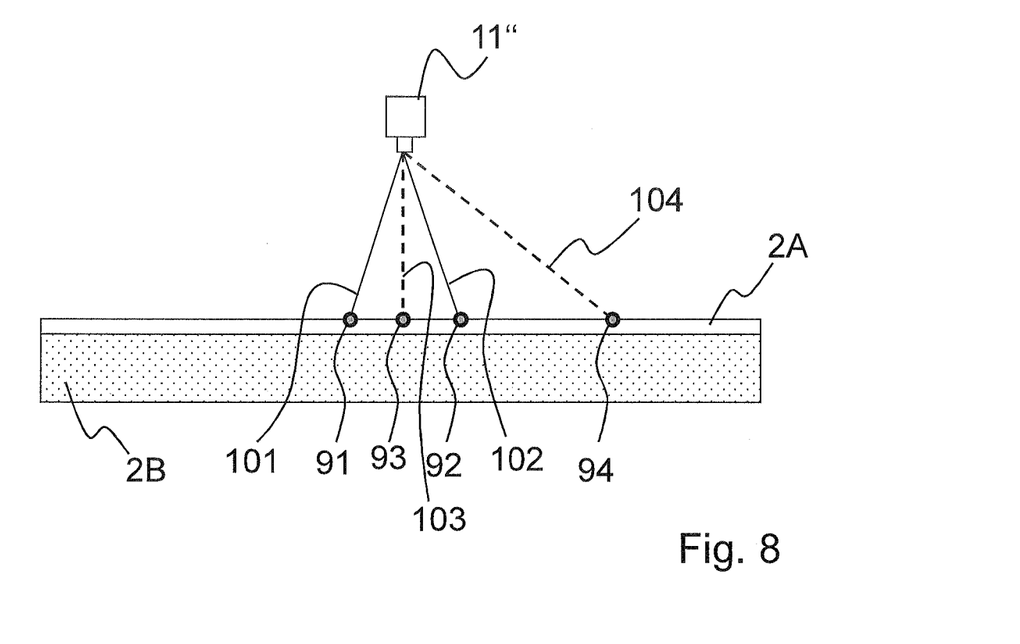
FIG. 8 depicts a third exemplary embodiment of a device according to the invention during the inspection of a uniformly coated material, in a view from the front.
Figure 9:
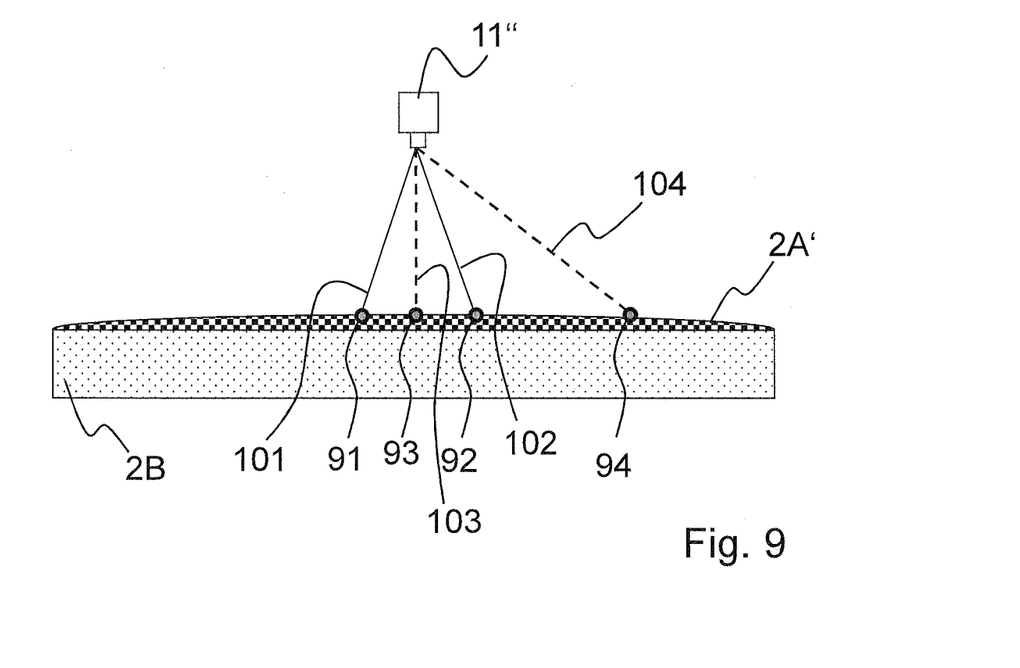
FIG. 9 depicts the exemplary embodiment according to FIG. 8 during the inspection of a material to be coated non-uniformly but symmetrically relative to the optical axis of the camera, in a view from the front.
Figure 10:
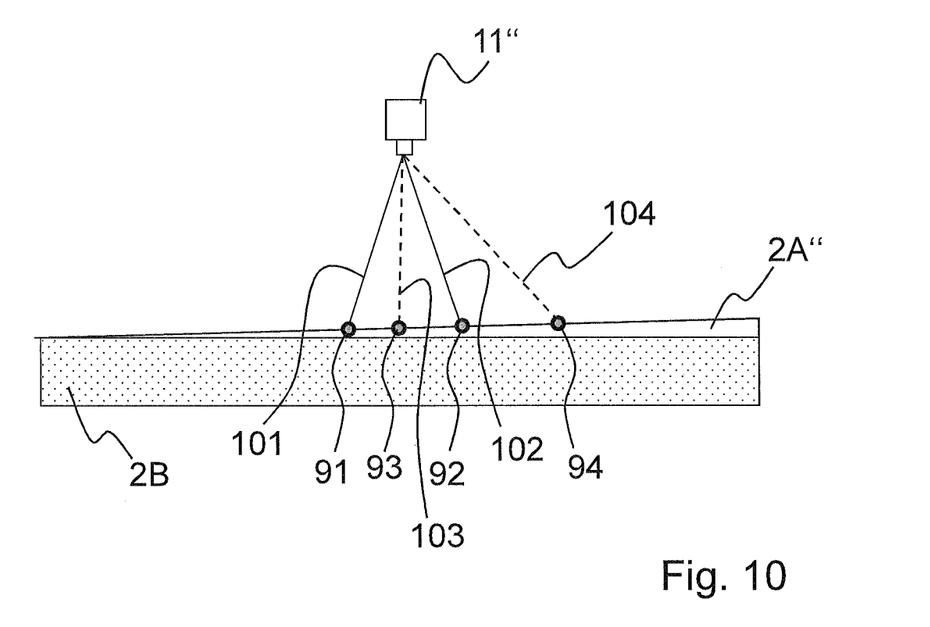
FIG. 10 depicts the exemplary embodiment according to FIG. 8 during the inspection of a material coated in the shape of a wedge, in a view from the front.

FIGS. 8 to 10 will be referred to in the following in order to describe what further statements can be made regarding the quality of a coating 2A of a glass material 2B using a device according to the invention having a single camera 11".

The camera 11" is situated perpendicularly above the glass material 2B provided with the coating 2A, 2A', 2A" and above the non-illustrated inspection line, which extends on the surface of the coating 2A, 2A', 2A" and has, inter alia, the points 91, 92, 93, 94. The camera 11" has an aperture that is so large that the glass material provided with the coating can be investigated by the camera 11" along the entire width thereof. The non-illustrated light source (see the explanations provided for FIG. 2) is disposed above the coated glass material, at a slant relative to the camera 11".

The conditions are simplest when the camera 11" looks down perpendicularly onto the coated glass material, as illustrated in FIGS. 8 to 10. Specifically, the camera 11" observes the light from the light source that is reflected at the points 91, 92 of the inspection line at the same viewing angle along the lines of sight 101 and 102. The light from the light source that is reflected at the points 93 and 94 is detected at various viewing angles along the lines of sight 103 and 104.

The coating 2A depicted in FIG. 8 has a uniform thickness, and therefore defect type 1 is not present. Given the same layer thickness and the same viewing angles (see points 91, 92 and lines of sight 101 and 102), the color values are the same. The color values can be different at different viewing angles (see points 92, 93, 94 and lines of sight 102, 103, 104). It cannot be unambiguously determined whether defect type 1 or 2 is present. It is only possible to identify a color deviation from the predefined setpoint value or setpoint value range. In particular, it not possible to investigate the entire surface with regard to the defect type 2, wherein at least two color values for different viewing angles are detected for each point of the coated glass, as can be carried out with the exemplary embodiments depicted in FIGS. 1 and 3.

FIG. 9, which follows, shows a non-uniform coating 2A', which is symmetrical with respect to the optical axis of the camera 11".

In this variant of a coating, identical color values are determined at identical viewing angles (see points 91, 92 and lines of sight 101 and 102), even though defect type 1 is present. Different color values are detected at different viewing angles (see points 92, 93, 94 and lines of sight 102, 103, 104). Defect type 2 can be identified in a manner analogous to FIG. 8 for two separate points, independently of the cause thereof.

The case of a wedge-shaped coating 2A" should also be considered, which is depicted in FIG. 10.

Different color values are determined at the same viewing angles (see points 91, 92 and lines of sight 101 and 102) and color values that are clearly different are detected at different viewing angles (see points 92, 93, 94 and lines of sight 102, 103, 104). In this coating variant as well, defect type 2 can be identified for two separate points, in a manner analogous to that depicted in FIG. 8, across the entire width independently of the cause thereof.

In all, the detection of a color deviation at different viewing angles is initially independent of defect type 1 or 2. If there are great color deviations along the inspection line or the surface of the coated material to be investigated, this is entirely unsuitable for a facade, for example.

A color deviation that is independent of the defect type can be easily determined with a camera having a corresponding aperture. Such a result is sufficient for many practical cases. In order to rule out defect type 1, however, at least two cameras must be used, which look at different points of the glass at the same viewing angle and determine that the color values are the same.

LIST OF REFERENCE CHARACTERS 1, 1' inspection line
2 glass with coating on the surface
2A, 2A', 2A" coating
2B material (glass)
3 arrow (moving direction)
5 carrier
11, 11', 11" first camera
12, 12' second camera
13, 13' third camera
14' fourth camera
15' fifth camera
16' sixth camera
18 light source
21 first aperture of the first camera 11
22 second aperture of the second camera 12
23 third aperture of the third camera 13
31, 32, 33 line of sight
41, 42, 43 line of sight
30, 40 point on inspection line 1
50 additional measuring device
61 axis (viewing angle in degrees)
62 axis (position of the point on the inspection line 1, 1' in millimeters)
71, 72, 73, 74, 75, 76 curve
81, 82, 83, 84, 85, 86, 87, 88, 89 curve
91, 92, 93, 94 point on the inspection line
101, 102, 103, 104 line of sight
$\alpha 1$, $\alpha 1'$ inclination angle of the first camera 11, 11' relative to the normal line on the surface
$\alpha 2'$ inclination angle of the second camera 12, relative to the normal line on the surface
$\alpha 4'$ inclination angle of the fourth camera 14', relative to the normal line on the surface
$\alpha 5'$ inclination angle of the fifth camera 15', relative to the normal line on the surface
b width of the inspection line 1
S normal line on the surface of the glass 2

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A device for inspecting a material provided with a coated surface, comprising:
   a light source disposed above the surface that emits light in a predefined wavelength range in the direction of the surface;
   at least one first camera disposed above a line located on the surface, tilted relative to the light source and configured with a first aperture for detecting light reflected from the surface at a first point on the line at a first viewing angle and detecting light reflected from the surface at a second point of the line, which is spaced apart from the first point, separately at a second viewing angle, wherein the second viewing angle is different than the first viewing angle, and wherein the camera determines a first color value of the light reflected by the first point and a second color value of the light reflected by the second point; and
   an evaluation device that is connected to the at least one first camera and compares the first color value and the second color value or a difference between the first color value and the second color value with a certain predefined color setpoint value or with a certain predefined color setpoint value range and evaluates the first color value of the light reflected by the first point of the line and the second color value of the light reflected by the second point of the line depending on the first and the second viewing angles, respectively.

2. The device according to claim 1, further comprising at least one second camera for determining a color value of the detected light, the second camera disposed above the line located on the surface, connected to the evaluation device, tilted relative to the light source and configured with a second aperture for detecting light reflected from the surface at each point of the line at a second viewing angle simultaneously with detection by the first camera, wherein the first camera and the second camera each determine the color value of the light reflected by each point of the inspection line, and wherein the evaluation device uses the color values determined by the first camera and the second camera to perform a comparison with the certain predefined color setpoint value or the certain predefined color setpoint value range.

3. The device according to claim 2, wherein the first camera and the second camera are disposed on a common carrier.

4. The device according to claim 2, wherein the first camera, the second camera or both are either a line scan camera or an area scan camera.

5. The device according to claim 2, wherein the material is moved relative to the first camera and the second camera and the light source in a feed direction, and wherein one or more of the light source, the first camera and the second camera are tilted in the feed direction or counter to the feed direction.

6. The device according to claim 2, further comprising at least one third camera for determining a color value of the detected light, the third camera disposed above the line located on the surface, tilted relative to the light source and configured with a third aperture for detecting reflected light at a third viewing angle and determining associated color value therefrom, at least for the points of the line in a certain range of the line, wherein the evaluation device compares the viewing angle of the third camera with the viewing angle of the first camera, the viewing angle of the second camera, or both, for each point of the certain range of the line and uses the two color values of the first camera, the second camera and the third camera determined respectively at the corresponding point of the certain region for the comparison with the certain predefined color setpoint value or the certain predefined color setpoint value range for which the difference of the associated viewing angle is greatest.

7. The device according to claim 6, wherein the evaluation device determines a color value difference of two color values of two of the first, second and third cameras that observe the light reflected from said corresponding point, at each point of the line, and compares the color value difference with a certain predefined color value difference setpoint value or a certain predefined color value difference setpoint range.

8. The device according to claim 1, wherein the first viewing angle and the second viewing angle differ by at least 10°.

9. The device according to claim 1, wherein the first viewing angle and the second viewing angle differ by at least 20°.

10. The device according to claim 1, wherein the first point and the second point are observed by the at least one first camera at the same or approximately the same viewing angle in different directions along the line.

11. A method for inspecting a material provided with a coated surface using a light source disposed above the surface that emits light in a predefined wavelength range in the direction of the surface and at least one first camera configured with a first aperture that detects light reflected from the surface to determine a color value of detected light, the first camera disposed above a line located on the surface and arranged at a slant relative to the light source, the method comprising the steps of:

using the first camera to separately detect the light from the light source that is reflected by a first point of the line at a first viewing angle and the light from the light source that is reflected by a second point of the line, which is spaced apart from the first point, at a second viewing angle to determine a first color value of the light reflected by the first point and a second color value of the light reflected by the second point; and using an evaluation device connected to the first camera to compare the first color value and the second color value or the difference between the first color value and the second color value with a certain predefined color setpoint value or a certain predefined color setpoint value range, to evaluate the first color value of the light reflected by the first point of the line and the second color value of the light reflected by the second point of the line depending on the first and the second viewing angles, respectively, and to evaluate the color value of the light reflected by the various points on the line depending on an associated viewing angle.

12. The method according to claim 11, where at least one third camera is disposed above the line located on the surface at a slant relative to the light source and configured with a third aperture, wherein the third camera:

detects light reflected detected by each point of the line simultaneously with the first camera and the second camera and determines an associated color value at least for the points of the line in a certain range of the line; and the evaluation device compares a viewing angle of the third camera with a viewing angle of the first camera, a viewing angle of the second camera, or both, for each point of the certain region of the line and, for the corresponding point of the certain region, compares the two color values of the first camera, the second camera and the third camera with the certain predefined color setpoint value or the certain predefined color setpoint value range for which the difference of the associated viewing angle is greatest.

13. The method according to claim 12, wherein the evaluation device determines a color value difference of two color values determined by any two of the first camera, the second camera and the third camera that observe the light reflected from this point, at each point of the line, and compares the color value difference with a certain predefined color value difference setpoint value or a certain predefined color value difference setpoint range.

14. The method according to claim 11, wherein at least one second camera is disposed above the line located on the surface, tilted relative to the light source and configured with a second aperture, wherein the second camera:

detects light reflected by each point of the line simultaneously with the first camera and determines a second color value of the detected light; and the evaluation device compares the first color value and the second color value with the certain predefined color setpoint value or the certain predefined color setpoint value range.

\* \* \* \* \*